United States Patent
Klee et al.

(10) Patent No.: US 10,751,495 B2
(45) Date of Patent: Aug. 25, 2020

(54) PATIENT INTERFACE

(71) Applicant: KONINKLIJKE PHILIPS N.V., Eindhoven (NL)

(72) Inventors: Mareike Klee, Straelen (DE); Nocolaas Petrus Willard, Valkenswaard (NL); Joyce Van Zanten, Waalre (NL); Lutz Christian Gerhardt, Eindhoven (NL); Veena Mohan, Cambridge (GB)

(73) Assignee: Koninklijke Philips N.V., Eindhoven (NL)

( * ) Notice: Subject to any disclaimer, the term of this patent is extended or adjusted under 35 U.S.C. 154(b) by 1073 days.

(21) Appl. No.: 15/105,626

(22) PCT Filed: Dec. 15, 2014

(86) PCT No.: PCT/EP2014/077665
§ 371 (c)(1),
(2) Date: Jun. 17, 2016

(87) PCT Pub. No.: WO2015/091304
PCT Pub. Date: Jun. 25, 2015

(65) Prior Publication Data
US 2016/0317771 A1    Nov. 3, 2016

(30) Foreign Application Priority Data
Dec. 20, 2013    (EP) .................................... 13198893

(51) Int. Cl.
*A61M 16/06*    (2006.01)
(52) U.S. Cl.
CPC ........ *A61M 16/0622* (2014.02); *A61M 16/06* (2013.01); *A61M 16/0633* (2014.02);
(Continued)

(58) Field of Classification Search
CPC .. A62B 9/00; A62B 9/04; A62B 9/006; A62B 18/00; A62B 18/02; A62B 18/08;
(Continued)

(56) References Cited

U.S. PATENT DOCUMENTS 4,155,358 A   5/1979 McAllister
4,488,547 A   12/1984 Mason
(Continued)

FOREIGN PATENT DOCUMENTS

AU   2007278766 A1   1/2008
CA    2820393 A1   6/2012
(Continued)

OTHER PUBLICATIONS

Ariani N. et al., "Microbial Biofilms on Facial Prostheses", Biofouling: The Journal of Bioadhesion and Biofilm Research, v 28, No. 6, pp. 583-591, Jul. 2012. http://dx.doi.org/10.1080/08927014.2012.698614.
(Continued)

*Primary Examiner* — Rachel T Sippel
*Assistant Examiner* — Benjamin M. Kusiak
(74) *Attorney, Agent, or Firm* — Michael W. Haas

(57) ABSTRACT

The present invention relates to patient interfaces optically indicating a user that a member of the patient interface needs to be replaced due to wear. In particular, the present invention relates to a member for patient interface which includes at least one functional material having a predefined functionality and at least one indicator wherein the concentration of the at least one indicator in the member correlates with the predefined functionality of the at least one functional material.

13 Claims, 7 Drawing Sheets

(52) U.S. Cl.
CPC ..... *A61M 16/0616* (2014.02); *A61M 16/0683* (2013.01); *A61M 2205/0205* (2013.01); *A61M 2205/0227* (2013.01); *A61M 2205/13* (2013.01); *A61M 2205/583* (2013.01); *A61M 2205/584* (2013.01)

(58) Field of Classification Search
CPC ........... A62D 5/00; A62D 7/00; A61M 16/00; A61M 16/06; A61M 16/0616; A61M 16/0622; A61M 16/0633; A61M 16/0683; A61M 2205/02; A61M 2205/0205; A61M 2205/0216; A61M 2205/0227; A61M 2205/0238; A61M 2205/013; A61M 2205/583; A61M 2205/584; A61M 2210/0606; A61M 2210/0625; A61K 31/01; A61K 31/02; C08K 5/42; C08L 83/04
USPC ............ 128/206.24, 202.22, 204.18, 205.25, 128/206.28, 206.21; 116/206; 283/114; 524/166, 588
See application file for complete search history.

(56) References Cited

U.S. PATENT DOCUMENTS

| | | | | |
|---|---|---|---|---|
| 5,219,341 | A * | 6/1993 | Serbiak | A61F 13/537 604/361 |
| 7,791,984 | B2 * | 9/2010 | Su | G01N 31/229 116/206 |
| 8,281,787 | B2 | 10/2012 | Burton | |
| 2004/0045551 | A1 * | 3/2004 | Eaton | A61M 16/06 128/206.21 |
| 2008/0006274 | A1 * | 1/2008 | Thornton | A61M 16/06 128/206.21 |
| 2008/0190432 | A1 | 8/2008 | Blochlinger et al. | |
| 2009/0120432 | A1 | 5/2009 | MacDonald | |
| 2009/0199857 | A1 * | 8/2009 | Peake | A61M 16/06 128/206.28 |
| 2010/0000534 | A1 | 1/2010 | Kooij | |
| 2010/0006101 | A1 * | 1/2010 | McAuley | A61M 16/06 128/206.24 |
| 2010/0018534 | A1 | 1/2010 | Veliss | |
| 2010/0280626 | A1 | 11/2010 | Shalon | |
| 2012/0079980 | A1 * | 4/2012 | Taylor | G01K 11/06 116/206 |
| 2012/0167816 | A1 * | 7/2012 | Chou | G01N 21/81 116/206 |
| 2012/0273000 | A1 * | 11/2012 | Jing | C09D 1/00 134/4 |
| 2013/0167305 | A1 * | 7/2013 | Weisman | D04H 3/00 8/137 |
| 2013/0190408 | A1 * | 7/2013 | Scholz | A61L 15/26 514/772.3 |
| 2013/0263352 | A1 * | 10/2013 | Crockett, Jr. | A41D 13/0015 2/69 |
| 2014/0005605 | A1 * | 1/2014 | Samade | C09D 129/04 604/131 |
| 2014/0034058 | A1 | 2/2014 | Resmed | |
| 2014/0109911 | A1 * | 4/2014 | Asvadi | A61M 16/06 128/205.25 |
| 2014/0303070 | A1 * | 10/2014 | Bjarnsholt | A61K 31/105 514/2.4 |
| 2014/0352602 | A1 * | 12/2014 | Manion | A61L 29/14 116/201 |
| 2015/0314098 | A1 * | 11/2015 | Allum | A61M 16/00 128/203.22 |
| 2016/0317771 | A1 | 11/2016 | Gerhardt et al. | |
| 2018/0360773 | A1 * | 12/2018 | Bjarnsholt | A61K 31/7036 |

FOREIGN PATENT DOCUMENTS

| | | |
|---|---|---|
| JP | H07315383 A | 12/1995 |
| JP | 2007127422 A | 5/2007 |
| RU | 2002116222 A | 2/2004 |
| WO | WO2008011682 A1 | 1/2008 |
| WO | WO2013001438 A1 | 1/2013 |
| WO | WO2013011478 A1 | 1/2013 |

OTHER PUBLICATIONS

Vissar A. et al., "Fate of Implant-Retained Craniofacial Prostheses: Life Span and Aftercare", International Journal of Oral and Maxillofacial Implants, pp. 89-98, v 23, No. 1, 2008.

Neu, T.R. et al., "Microflora on Explanted Silicone Rubber Voice Prostheses: Taxonomy, Hydrophobicity and Electrophoretic Mobility", Journal of Applied Bacteriology, v 76, pp. 521-528, 1994.

Neu, T.R. et al . . . , "Biodeterioration of Medical-Grade Silicone Rubber used for Voice Prostheses: a SEM Study", Biomaterials, v 14, No. 6, pp. 459-464, May 1993.

Kaali, P. et al., "Prevention of Biofilm Associated Infections and Degradation of Polymeric Materials used in Biomedical Applications", Chapter 22, in: Biomedical Engineering, Trends in Materials Science, pp. 513-540, Jan. 2011.

Galloway W.R.D. et al., "Quorum Sensing in Gram-Negative Bacteria: Small-Molecule Modulation of AHL and AI-2 Quorum Sensing Pathways", Chemical Reviews, v 111, No. 1, pp. 28-67, 2011.

Jakubovics, N.S., "Talk of the Town: Interspecies Communication in Oral Biofilms", Molecular Oral Microbiology, 25 (2010) 4-14 [a] 2010 John Wiley & Sons A/S, 2010.

Jakubovics, N.S. et al., "The Road to Ruin: the Formation of Disease-Associated Oral Biofilms", Invited Medical Review, Oral Diseases, pp. 1-11, 2010.

El Abed S. et al., "Scanning Electron Microscopy (SEM) and Environmental SEM: Suitable Tools for Study of Adhesion Stage and Biofilm Formation", Chapter 35 In: Scanning Electron Microscopy (edited by V. Kazmiruk), pp. 718-730, Mar. 2012, http://www.intechopen.com/books/scanning-electron-microscopy,(2012).

* cited by examiner

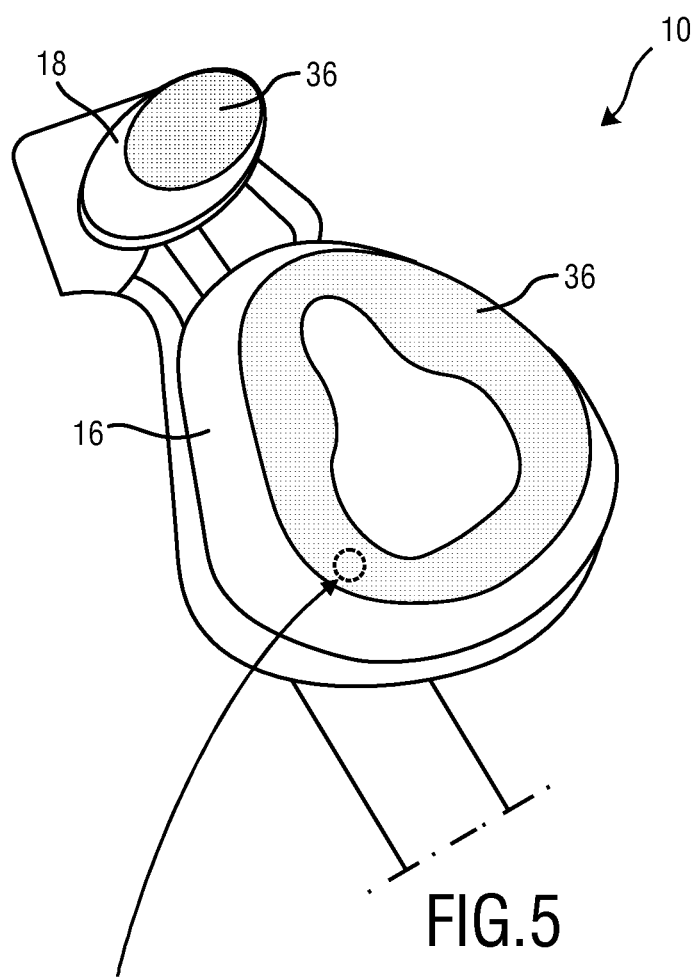
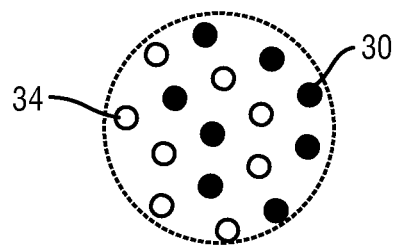
FIG.5
FIG.6

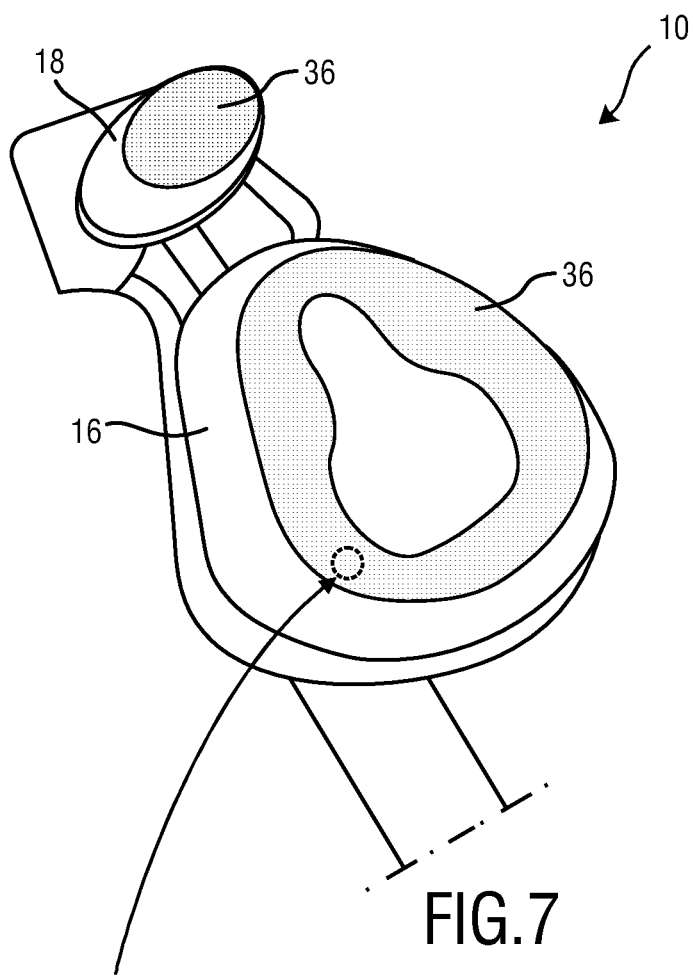
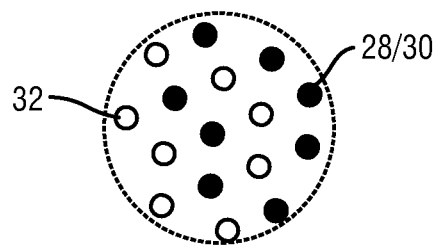
FIG.7
FIG.8

PATIENT INTERFACE

CROSS-REFERENCE TO RELATED APPLICATIONS

This patent application claims the priority benefit under 35 U.S.C. § 371 of international patent application no. PCT/EP2014/077665, filed Dec. 15, 2014, which claims the benefit of European Patent Application No. EP13198893.3, filed on Dec. 20, 2013, which is hereby incorporated by reference herein.

FIELD OF THE INVENTION

The present invention relates to a member of a patient interface which indicates (preferably visually) a user that the member and/or the patient interface needs to be replaced due to long-term usage and related functionality changes of materials. Further, the present invention relates to a patient interface including such a member.

BACKGROUND OF THE INVENTION

Patient interfaces, such as masks in pressure support systems, are used for delivering gas to a user. Such gases like air, cleaned air, oxygen, or any modification thereof are submitted to the user (also referred to as patient) via the patient interface in a pressurized or unpressurized way.

For several chronic disorders and diseases the usage of such a patient interface is necessary or at least advisable.

One example of such a disease is obstructive sleep apnea or obstructive sleep apnea syndrome (OSA). OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface, e.g. a face mask, is attached to a tube and a machine that blows pressurized gas, preferably air, into the patient interface and through the airway of the patient in order to keep it open. Positive air pressure is thus provided to a patient through a hose connected to a patient interface or respiratory interface, such as a face mask, that is worn by the patient regularly at night. The afore-mentioned long-term use of the patient interface is the result, since the wearing of the patient interface usually takes place during the sleeping time of the patient.

Examples for patient interfaces are:
nasal masks, which fit over the nose and deliver gas through the nasal passages,
oral masks, which fit over the mouth and deliver gas through the mouth,
full face masks, which fit over both, the nose and the mouth, and deliver gas to both, and
nasal pillows, which are regarded as masks as well within the scope of the present invention and which consist of small nasal inserts that deliver the gas directly to the nasal passages.

In order to guarantee a reliable operation of the device, the patient interface needs to closely fit on the patient's face to provide an air-tight seal at the mask-to-face interface. Usually, the patient interface is worn using a head gear with straps that go around the back of the patient's head. The patient interface or mask in practice usually comprises a soft cushion that is used as mask-to-patient interface, i.e. that contacts the face of the patient when the mask is worn, as well as it usually comprises a so-called mask shell building a rigid or semi-rigid holding structure for holding the cushion in place and for supplying mechanical stability to the patient interface.

The cushion usually comprises one or more pads made of gel or silicone or any other soft material in order to increase the patient comfort and guarantee a soft feeling on the patient's face. The latter-mentioned mask shell usually also comprises a hose interface that is adapted for connecting the air supplying hose to the mask. Depending on the type of the mask, it may also comprise a mechanism with an additional cushion support on the forehead to balance the forces put by the mask around the airway entry features of the human face.

Since the above-mentioned patient interfaces are usually worn over night and on a long-term basis, it is evident that e.g. cleaning of the patient interface is, especially for hygienic reasons, of great importance. It is therefore desirable that the patient interface may be disassembled into different parts in order to ease the cleaning of the patient interface. In addition, parts of the patient interface, such as cushions, have to be replaced frequently as they can wear out as a consequence of material degradation over time. These parts of the patient interface which are in immediate contact with the skin may contain compounds having a predefined functionality such as compounds assisting in avoiding skin infection or skin irritations, in particular redness, or skin damage/breakdown due to regular long-term usage of the patient interface. Examples of these compounds comprise moisture uptake means and anti microbial agents. These compounds are however subjected to loss and/or decomposition with the consequence that the mask or parts thereof require substitution.

In the art difficulties relating to the question when a device or parts thereof need replacement due to wear have been addressed to by providing devices providing an indication that after a predefined time limit replacement of the device is required.

US 2009/0199857 A1 informs about such a mask including a patient interface and a reminder system provided to the patient interface. The reminders may be based on chemicals and changes in appearance on parts of the mask itself. Chemicals may be provided indicating after a predetermined period of time that replacement is required.

U.S. Pat. No. 4,488,547 A discloses a surgical mask which changes color to signal a significant loss of bacterial filtration efficiency due to moisture accumulation. Said mask has a layer of a bacterial filtration material of a first color. A hygroscopic material partially covers a surface of said layer of filtration material and serves for the absorption of water from respired air. Absorption causes said hydroscopic material to change color to a second color not identical to said first color. Color change from said first color to said second color indicates that replacement of the mask is required.

US 2010/0018534 A1 refers to a patient interface, wherein the interface material may be made of a foam acting as heat and moisture exchanger. It is further mentioned that the foam structure may have a certain usage life or lifespan. The foam structure may include an end-of-life indicator to indicate that the end of usage life has been reached.

U.S. Pat. No. 4,155,358 pertains to a disposable valveless chemical cartridge respirator for filtration of vinyl chloride monomer. The cartridge has an end of service life indicator. The indicator system is based on potassium permanganate changing its color due to the reductive influence of vinyl chloride.

The systems of the state of the art for indicating that the replacement is required exhibit essentially the same drawbacks. Both prior art documents rely on external factors for determining span of life of the devices. Said factors however are not directly reflecting properties of the material undergoing wear out along with material functionality change, i.e., with the consequence that the remaining span of live of the devices may not be exactly ascertained, but only roughly estimated.

SUMMARY OF THE INVENTION

It is therefore an object of the present invention to provide patient interfaces or components thereof reliably showing the user that replacement is required. Another objective of the present invention recites in the provision of a patient interface or component thereof accurately indicating its remaining span of life.

In a first aspect of the present invention a member for patient interfaces is provided. Said member comprises at least one functional material having a predefined functionality and at least one indicator, wherein concentration of said at least one indicator in said member correlates with the predefined functionality of said at least one functional material, wherein said at least one functional material and said at least one indicator are arranged in a skin contacting material.

In a further aspect of the present invention a patient interface for delivering gas to a user is presented, said patient interface comprises the present member.

The invention therefore overcomes the above-mentioned disadvantages by providing a member or a patient interface comprising such a member wherein one or more indicators, such as color indicators, are employed. The concentration(s) of said one or more indicators correlate(s) with the predefined functionality of said at least one functional material. The present inventors have found that the loss of the predefined functionality of a material, such as an active compound, by e.g. washing out or decomposition may be easily correlated to the concentration of the indicator. In case a colored indicator is employed as indicator, a color change indicates when the predefined functionality is either completely or partially lost. For this purpose color wheels or color diagrams may be provided permitting the user to assess wear out of the member qualitatively by comparison of the actual color of the member with the colors of the color wheel or colored diagram. This permits in turn immediate assessment of the condition of the member/patient interface by indicating for example that the device is either new or needs replacement. It is even possible to quantitatively indicate the remaining span of life by indicating a time specification, such as several days or weeks. This may be obtained by assigning the actual color of the indicator to a color wheel or a colored diagram containing indications referring to a time specification which may be indicated in terms of days or weeks. As the remaining span of life is subjected to different external factors, such as UV radiation, inappropriate storage conditions or user dependent sebum levels, the time specification indicated may be also in form of a time frame.

A member as used herein may be understood as any component of a patient interface. It particularly addresses to components which are either in direct contact with the skin of the user upon wearing the same or in close vicinity thereto. The member may be for instance the cushion or the skin contacting material (SCM) formed or made thereon. The member may also correspond to the mask shell and/or forehead support. The member may be processed by a variety of materials including hydrophilic silicones, for instance Elastosil LR3004/40 filled with alpha olefin sulfonate. It will be appreciated that the member is not limited to patient interfaces but may be also employed in other body-worn devices such as head sets.

A functional material having a predefined functionality addresses essentially each kind of active compounds, such as drugs, prodrugs, or skin oils, including of which may be beneficial for the user upon wearing the member/patient interface.

The functional material may be a compound added to the material forming said member. Examples of such functional materials comprise inter alia an alpha olefin sulfonate or a quorum sensing inhibitor. Said functional materials may be in form of molecules which may be embedded in the material forming the member.

The patient interface may for example have a first member which is connected with a second member, said first member comprising a cushion for contacting a face of the user, and wherein the second member comprises a mask shell for holding the cushion. Said cushion has a skin contacting material (SCM). The skin contacting material (SCM) may be also denominated skin contacting material (SCM) part or sealing flap herein. The skin contacting material (SCM) of the cushion or alternatively said cushion comprises at least one functional material having a predefined functionality and at least one indicator, wherein concentration of the at least one indicator in said cushion correlates with the predefined functionality of said at least one functional material.

Preferably, the functional material may be a constituent of said member. In this case at least a part of the member or the complete member is made of the functional material. Examples of such functional materials being a constituent of said member comprise inter alia a hydrophilic material that absorbs water or a hydrophilic material formed with capillaries as outlined in the instant application.

It will be appreciated that combinations of any kind of functional materials are encompassed by the present invention. Examples comprise a member made of hydrophilic material formed with capillaries, to which alpha olefin sulfonate and/or a quorum sensing inhibitor has been added.

An indicator or a mask wear out indicator may be each kind of chemical substance which may be either colored per se or undergoes a color change upon an external influence. In principle each dye may be used for putting the present invention into practice. The color change of the mask to be used as wear out indicator allows the user visual control and feedback on the mask functionality. In addition a color wheel may be used permitting comparison and facilitating the actual wear out condition and remaining life-span of the mask. Alternatively, the color change may be validated employing digital color measurements. At least one indicator is directed to any number of indicators, such as 1 to 10 indicators, preferred are 5, 4, 3, 2 indicators or 1 indicator.

The concentration of said indicator is usually positively correlated with the predefined functionality of said material. This means that any decrease of the predefined functionality in said member, either by washing out, decomposition, (chemical) modification, or any other event causing loss of functionality of said material, involves diminishing of the concentration of the indicator. This decrease in concentration may be usually easily followed by the user and permits a qualitative or quantitative assignment to the actual rate of wear.

Said at least one functional material having a predefined functionality and said at least one indicator may be arranged in one or more of the following a skin contacting material (SCM) of the member, a cushion for contacting a face of the user, a forehead support, and a mask shell. As outlined above, the member may be understood as any component of a patient interface, particularly those which are either in direct contact with the skin of the user upon wearing the same or in close vicinity thereto. It will be appreciated that the member is not limited to patient interfaces but may be also employed in other body-worn devices such as head sets. Alternatively, said functional material having a predefined functionality and/or said at least one indicator is inherent in the material forming of one or more of the following the skin contacting material (SCM) of the member, a cushion for contacting a face of the user, a forehead support, and a mask shell.

At least one functional material is directed to any number of functional materials, such as 1 to 10 functional materials, preferred are 5, 4, 3, 2 functional materials or 1 functional material. At least one indicator is directed to any number of indicators, such as 1 to 10 indicators, preferred are 5, 4, 3, 2 indicators or 1 indicator.

In general each number of indicators and functional materials may be employed in the present patient interface or present member for patient interfaces. For example, 3 indicators and 3 functional materials, 3 indicators and 2 functional materials, 2 indicators and 3 functional materials, 2 indicators and 2 functional materials, 2 indicators and 1 functional material, 1 indicator and 2 functional materials. Preferred is a combination of 1 indicator and 1 functional material. An alternative is a combination of 1 indicator and 2 functional materials, such as a member made of hydrophilic material formed with capillaries, containing an indicator, such as Fast Green FCF, and alpha olefin sulfonate or a quorum sensing inhibitor. Another alternative is a combination of 1 indicator and 3 functional materials, such as a member made of hydrophilic material formed with capillaries, containing an indicator, such as Fast Green FCF, alpha olefin sulfonate and a quorum sensing inhibitor.

Said skin contacting material (SCM) represents the part of the member of the patient interface forming the immediate contact between the patient interface and the human skin upon wearing by a user. The skin contacting material (SCM) may have a certain layer thickness of 0.1 to 5 mm, preferably from 0.1 to 4 mm, from 0.1 to 3 mm, from 0.1 to 2 mm, from 0.1 to 1 mm, from 0.1 to 0.5 mm, from 0.1 to 0.4 mm, or from 0.2 to 0.4 mm. More preferred is a layer thickness of 0.3 to 0.4 mm such as 0.31, 0.32, 0.33, 0.34, 0.35, 0.36, 0.37 0.38 or 0.39 mm. Said at least one functional material having a predefined functionality and said at least one indicator are usually embedded or evenly distributed in said skin contacting material (SCM). This means that the molecules or function of said at least one functional material having a predefined functionality and said at least one indicator have on average essentially the same distance to each other.

According to another embodiment of the present invention, said at least one functional material having a predefined functionality comprises a moisture uptake means and/or an anti microbial agent.

The moisture uptake means can be provided by a variety of materials or material systems such as a hydrophilic material that absorbs water, a hydrophilic material formed with capillaries which take up water, etc. The take up of water into the material can result in softening or weakening of the material and the support material has the purpose of supporting such weakened material. Hence the moisture uptake means can comprise a hydrophilic material or a hydrophobic material depending on how it is structured and used. The hydrophilic material may be a textile integrated in the contact structure. Preferably such a material is adapted so that said textile at said skin surface of a user is crease-free and/or leak-free. The hydrophilic material can be a rubber material that takes up at least 5% by weight of water, preferably more that 10% by weight of water and particularly preferably more than 40% up to 120% by weight of water, or up to 200% or up to 250% or up to 500% by weight of water after immersion in demineralized water at room temperature for a sufficient time such as 5 days or more to reach saturation. It is expected that with increasing water absorption the mechanical properties may be reduced such that a support material is not only necessary but must be designed in a form that will stabilize the hydrophilic material.

The inclusion of moisture uptake means generally exhibit the problem that regular washing, usually at least once every day, of the patient interface, in particular the parts contacting the skin, i.e. cushion/member or at least the member skin contact area, is required. After a timeframe of typically 60-180 days and standard washing procedures provided by the manufacturer, the moisture controlling properties of a patient interface made of hydrophilic polymers with the hydrophilic material mixed into the polymer are nearly lost. After essentially the same timeframe the capillaries in a patient interface made of hydrophobic material are suspected to be covered with sebum. This results in the effect that the patient has increase moisture accumulation underneath the cushion or member of the mask and chance of increased red mark formation which may be effectively prevented by using the present patient interface or member for a patient interface.

The presence of anti microbial agents is intended to address contamination caused by undesired microorganisms, in particular microorganisms present in human skin, such as different kind of bacteria and yeasts. Anti microbial agents comprise inter alia quorum sensing inhibitors and antibiotics, but also other substances toxic for particular microorganisms, such as finely divided silver and detergents.

According to still another embodiment of the present invention, said moisture uptake means is a hydrophilic material.

The hydrophilic material is preferably a rubber material. The rubber material can be any of silicone, latex, and polybutadiene or other materials as disclosed below.

The hydrophilic polymer material, e.g. a hydrophilic rubber or elastomeric material, may exhibit improved moisture uptake properties, e.g. a hydrophilic silicone rubber material, which is capable of taking up more than 5% by weight of water, preferably more than 10% by weight of water, more preferably more than 20% by weight of water, most preferably more than 40% by weight of water, and up to 500% by weight, or up to 200%, or up to 120% by weight, of water after immersion in demineralized water at room temperature for a sufficient time such as 5 days or more to reach saturation. Such water-absorbing rubbery or elastomeric polymer materials, in particular hydrophilic silicone rubber materials, may be in the form of a sheet, or a coating adapted to be applied to a substrate, or foam, or a fiber, or any other form suitable for including into a medical or non-medical device where significant water-absorbing properties are desirable.

Alternatively, hydrophilic polymer materials, e.g. hydrophilic rubber or elastomeric materials, other than a hydrophilic silicone rubber material may be provided. This may be achieved for example by providing a hydrophilic polyurethane. Examples of such hydrophilic compounds to be mixed into the silicone or polyurethane are for example alpha olefin sulfonate, monomers or pre-polymers including, but are not limited to, glycerol, ethylene glycol derivatives, polyethylene glycol and other hydroxyl function-containing polyol compounds. Other examples of hydrophilic polymers that can be mixed into the silicone or polyurethane, etc., include, but are not limited to: polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof. Still other examples of hydrophilic polymers include hydrophilic polyether block amide copolymers.

The hydrophilic polymer material, e.g. a hydrophilic rubber or elastomeric material, may exhibit improved moisture uptake properties, e.g. a hydrophilic silicone rubber material, which is capable of taking up more than 5% by weight of water, preferably more than 10% by weight of water, more preferably more than 20% by weight of water, most preferably more than 40% by weight of water, and up to 500% by weight, or up to 200%, or up to 120% by weight, of water after immersion in demineralized water at room temperature for a sufficient time such as 5 days or more to reach saturation. Such water-absorbing rubbery or elastomeric polymer materials, in particular hydrophilic silicone rubber materials, may be in the form of a sheet, or a coating adapted to be applied to a substrate, or foam, or a fiber, or any other form suitable for including into a medical or nonmedical device where significant water-absorbing properties are desirable.

With respect to hydrophilic silicone rubber materials, there is no limitation upon the manufacturing method by which they may be obtained, that is any of the three crosslinking methods briefly mentioned above and further detailed hereinafter may be suitable, depending upon the medical or non-medical application for which the hydrophilic silicone rubber material is intended, and depending the form (e.g. sheet, coating, fiber or foam) in which the water-absorbing silicone rubber material is desired.

The present invention relates to hydrophilic silicone-based rubber materials having such high water uptake capacity at preferably room temperature that they can be used for manufacturing skin-friendly materials, in particular skin-contact products with a moisture regulation or moisture management function. The water-absorbing (hygroscopic) silicone-based rubber materials may be suitable for contact with human skin and water containing soft tissues but also hard tissues covered by fluid/water filled viscoelastic films (e.g. tooth pellicle).

Alternatively, hydrophilic polymer materials, e.g. hydrophilic rubber or elastomeric materials, other than a hydrophilic silicone rubber material may be provided. This may be achieved for example by providing a hydrophilic polyurethane. Examples of such hydrophilic compounds to be mixed into the silicone or polyurethane are for example alpha oelfin sulfonate, monomers or pre-polymers include, but are not limited to, glycerol, ethylene glycol derivatives, polyethylene glycol and other hydroxyl function-containing polyol compounds. Other examples of hydrophilic polymers that can be mixed into the polymers such as silicone, polyurethane . . . include, but are not limited to: polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof. Still other examples of hydrophilic polymers include hydrophilic polyether block amide copolymers.

In any of the embodiments of the present invention the hydrophilic material moisture uptaking means, or any other part of the device, may include one or more antibacterial agents, and/or one or more anti fungal agents such as silver compounds, or one or more anti-viral agents such as a microbiocide, all or any of these being for instance present in, or coated onto, any material in contact with the skin of the user.

According a preferred embodiment of the present invention, said hydrophilic material is an alpha olefin sulfonate containing/filled silicone rubber.

Introduction of an alpha-olefin sulfonate surfactant into the polymers forming the patient interface, cushion or member may provide a mixture with an increased hydrophilic character which can be used to increase its capacity to hold water. For the manufacture of skin-contact products, this is especially relevant to biocompatible polymers such as, but not limited to, silicones, polybutadiene, polybutadiene-containing polymers, polybutadiene-polyethylene oxides copolymers, poly(meth)acrylates, and isobutylene-ethylene glycol copolymers.

According to still another preferred embodiment of the present invention, said anti microbial agent is a quorum sensing inhibitor. The quorum sensing inhibitor may target one or more of the following:
a) the signaling mechanisms for the production of signals;
b) the signaling molecule itself;
c) the receptor.

Alternatively the quorum sensing inhibitor targets:
compounds or analogues that modulates the quorum sensing pathway; or
compounds or ligands that modulate the regulatory proteins; or
natural substances, such as extracts from plants and food or from alga; or
compounds that inhibits quorum sensing by competitively binding to the receptor site, such as furanones and structural analogues thereof; or
synthetic compounds; or
recognized drugs, such as macrolide antibiotics; or
non-native agonist or antagonists of known signaling molecules or precursors that are capable of modulating receptor activity. Accordingly, quorum sensing inhibitors may be discovered employing one or more of the above mentioned criteria.

Often infections are caused by bacteria which proliferate, sense/detect the density of bacterial species and alter the metabolism of individual members of a population as a result of that density. This process of communication within a population is termed as Quorum sensing (QS). Quorum sensing inhibitors are a big class of molecules which work by acting as an inhibitor for intercellular communication between bacteria thereby suppressing the formation of biofilms. Blocking the microbial communication could prevent the expression of many genes involved in the symbiosis of microbes with its own species as well with other species, inhibits biofilm formation, antibiotic production, and expression of virulence factors, etc. Synthetic compounds have also been found to be effective in quenching the quorum sensing system. Said quorum sensing inhibitors exhibit a potential for preventing and treating bacterial infections.

Examples of quorum sensing inhibitors suitable for use in the present invention comprise halogenated furanone compounds or furanone derivatives in general, but also other nonfuranone quorum sensing compounds are encompassed by the present invention. Halogenated furanone compounds or furanone derivatives are however preferred.

Following furanone derivatives are preferred in using as an anti microbial agent:

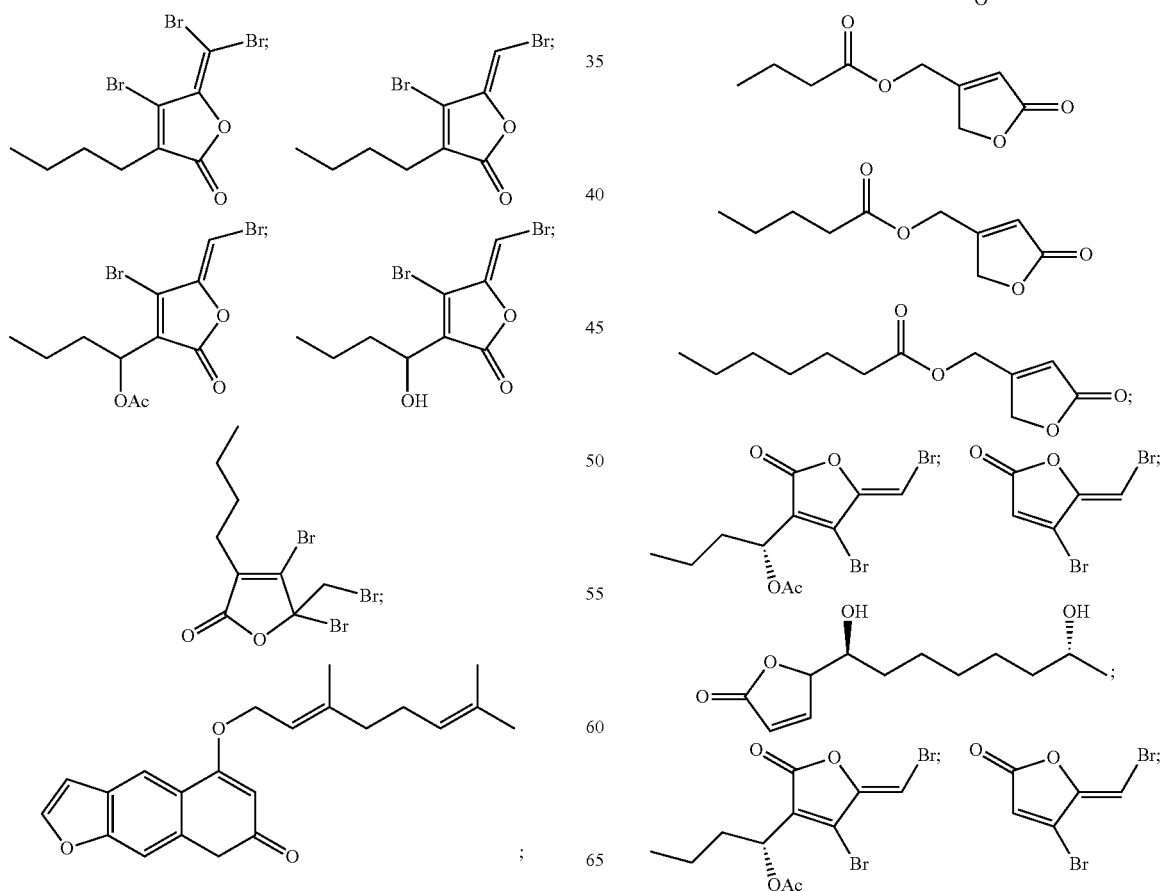

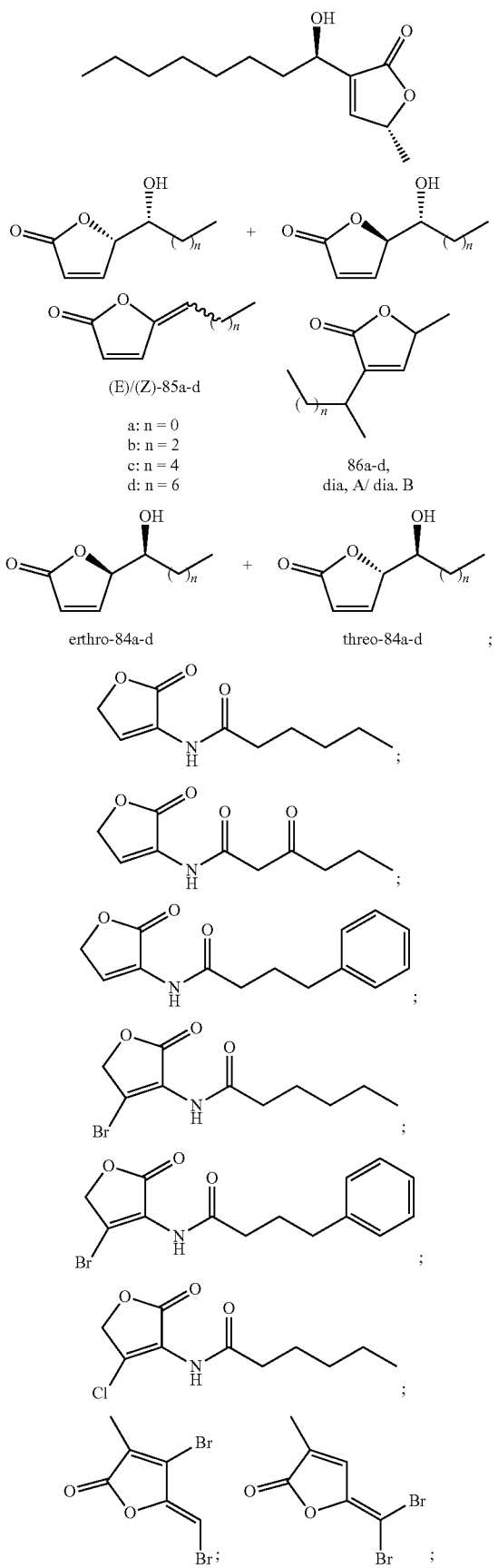

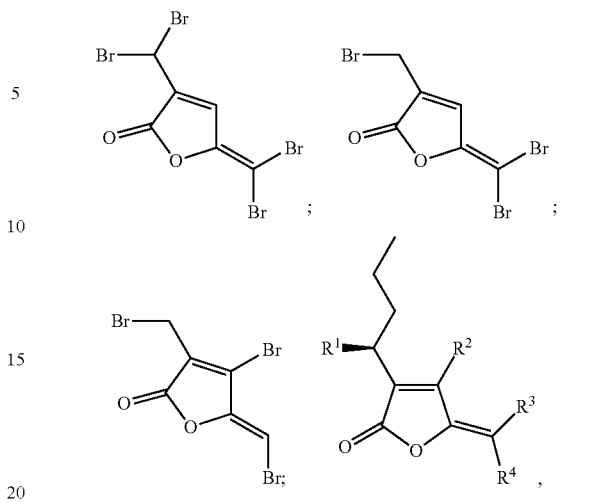

wherein $R^1$ is H, OH or OAc, $R^2$ and $R^3$ are independently from each other Br or H, and $R^4$ is Br or I, preferably $R^1$ is H, $R^2$, $R^3$, $R^4$ are each Br; or $R^1$ and $R^3$ are each H, $R^2$ and $R^4$ are each Br; or $R^1$ is OAc, $R^2$ and $R^4$ are each Br, $R^3$ is H; or $R^1$ is OH, $R^2$ and $R^4$ are each Br, $R^3$ is H; or $R^1$ is OAc, $R^2$ is Br, $R^3$ is H, $R^4$ is I; or $R^1$ and $R^2$ are each H, $R^3$ and $R^4$ are each Br; or $R^1$ is OAc, $R^2$, $R^3$, $R^4$ are each Br.

Following nonfuranone quorum sensing compounds are preferred in using as an anti microbial agent:

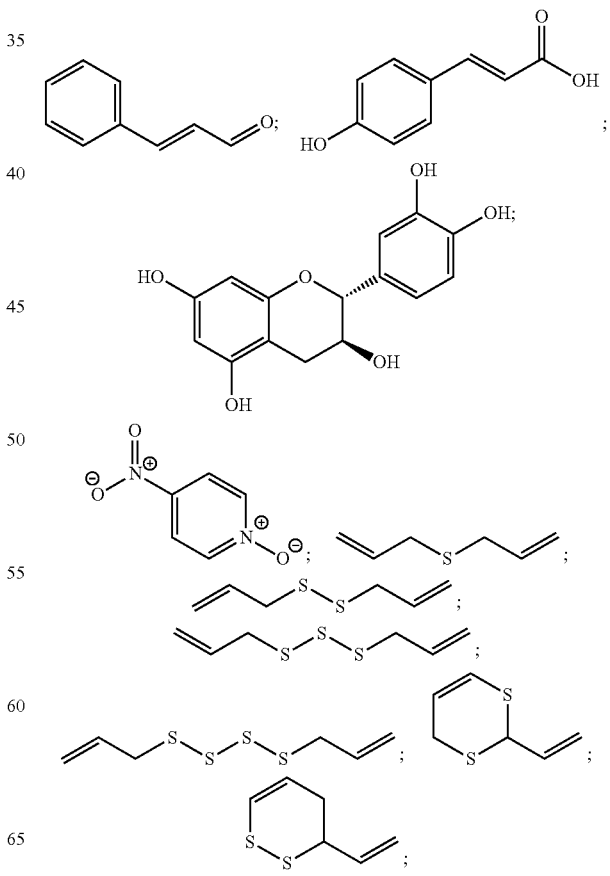

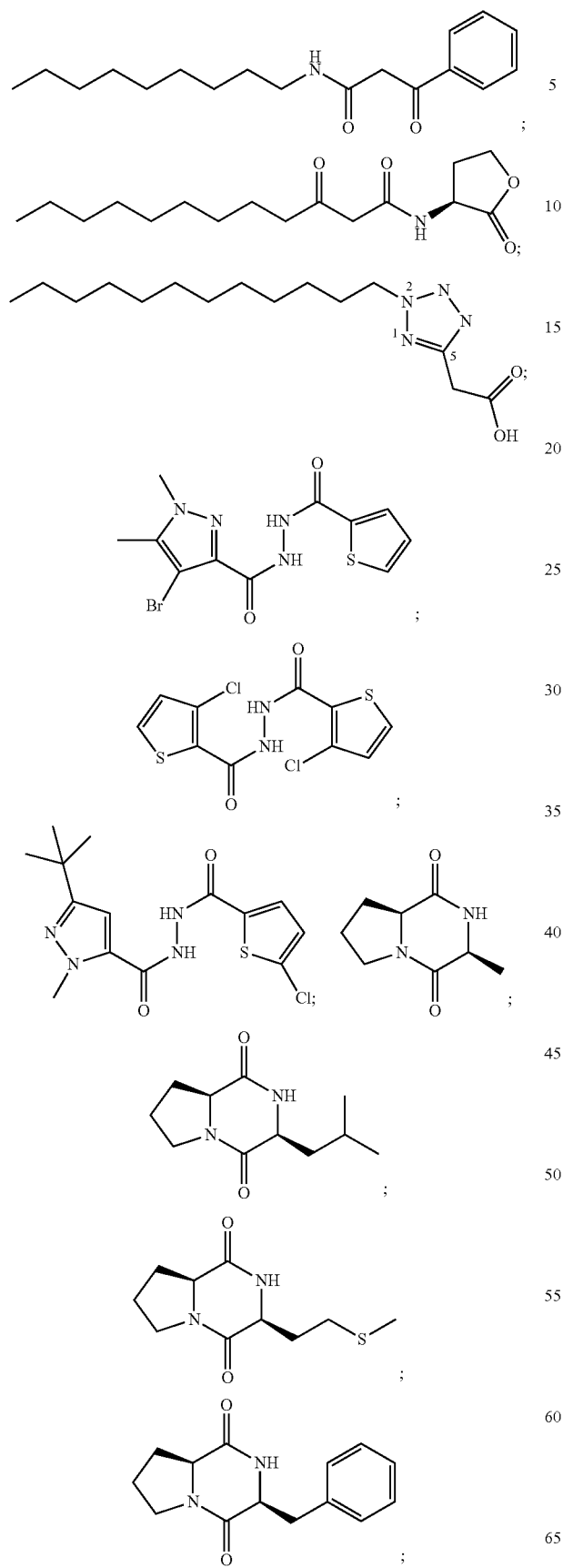
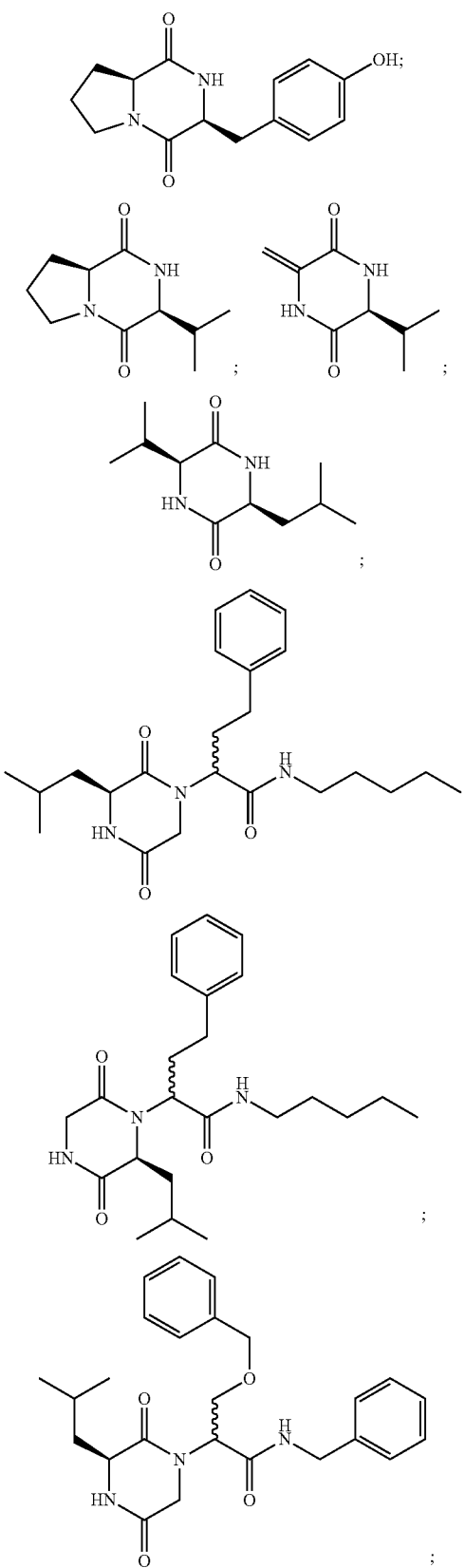

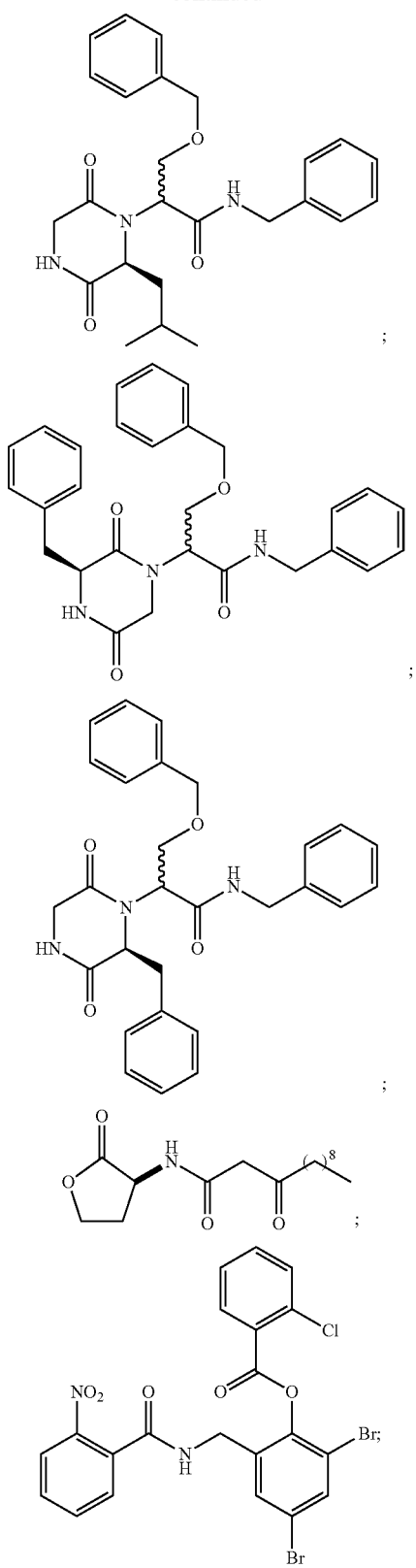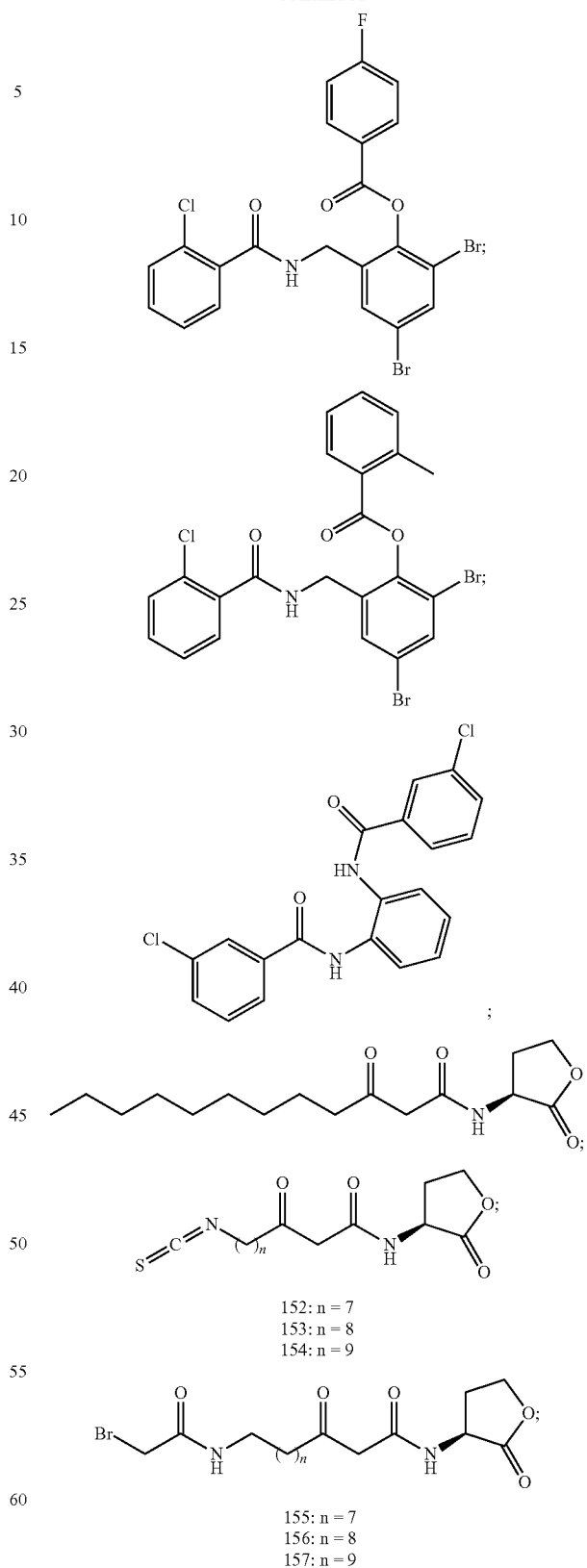

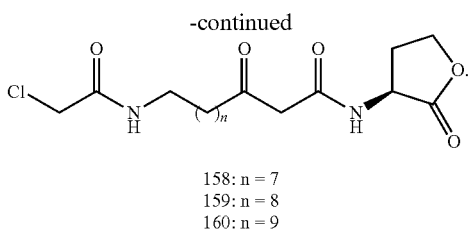

158: n = 7
159: n = 8
160: n = 9

According to an embodiment of the present invention, said at least one indicator is a colorant.

The colorant may be essentially each kind of chemical substance exhibiting a color. It will be appreciated that the intensity of the color depends on the concentration of the colorant as well as its chemical poverties. Likewise the functional material having a predefined functionality the colorant may be evenly distributed in said member. In this case the decrease in predefined functionality may be based essentially on the same mechanism like the loss of concentration of said at least one indicator. This means that the material with a predefined functionality may be washed out, i.e. the reason may be a diffusion based mechanism or decomposition. The same holds true for the indicator which is washed out together with the functional material having a predefined functionality or decomposes in parallel to said functional material having a predefined functionality. The colorant may be chemically linked to the functional material having a predefined functionality. Alternatively the colorant may be associated with the functional material having a predefined functionality either by van der Waals forces or hydrogen bonds. It is also possible that the colorant does not exhibit any inter molecular or intra molecular interaction with the functional material having a predefined functionality.

As colorant the hydrophilic compound mixed into the polymer, such as the alpha olefin sulfonate mixed into the silicone, can be used.

Other groups of suitable colorants comprise: Acid Blue 7 (CI 42080, 656840); Acid Blue 80; Acid Yellow 17 Alizarine Cyanine Green W.-S., D&C Green No. 5; Allura Red AC, FD&C Red No. 40; Amaranth, Naphthol Red S (E 123); Anthralan Violet 3B; Anthraquinone Dyes, such as Carmine, Alizarine Cyanine Green, Irisol, Acid Blue 80; Azorubine, Carmoisine (E 122); Beetroot Betanin (E 162); Brilliant Acid Green BS, Wool Green S, Lissamin Green BS (E142); Brilliant Black PN (E 151); Brown FK (E 154); Brown HT, Chocolate Brown HT (E 155); Carmine, Cochineal, Carminic Acid (E 120); Erythrosine (E 127); Fast Green FCF, FD&C Green No. 3; Fast Yellow (previously E 105); Indigotine (E 132); Orange II, D&C Orange No. 4; Orange Yellow S, Sunset Yellow FCF, FD&C Yellow No. 6 (E 110); Patent Blue VF, Amido Blue VF; Phloxine; Ponceau 4R, Cochineal Red A (E 124); Ponceau SX, FD&C Red No. 4; Pyranine, D&C Green No. 8; Quinoline Yellow (E 104); Red 10B, D&C Red No. 33; Sulforhodamine B; Tartrazine, FD&C Yellow No. 5 (E 102); and Uranin, Fluorescein Sodium. It has been found that these colorants are particularly suitable for hydrophilic silicone. Said colorants are non-charged or negatively charged. They do not form water insoluble products and exhibit low toxicity. Washing of the mask may be performed with anionic detergents.

Another group of suitable colorants comprises: Anthocyanin; Enocyanin (E 163); and Methyl Violet B. It has been found that these colorants are particularly suitable for hydrophilic silicone. Said colorants are non-charged or positively charged. They do not form water insoluble products and exhibit low toxicity. Washing of the mask may be performed with cationic detergents.

A further group of suitable colorants comprises: all above mentioned dyes; Ribovlavin; and Lactoflavin (E 101i). It has been found that these colorants are particularly suitable for hydrophilic silicone. Said colorants are non-charged, positively or negatively charged. They do not form water insoluble products and exhibit low toxicity. Washing of the mask may be performed with non-ionic detergents.

A further group of suitable colorants comprises: Alizarine Cyanine Green F.-S.; Annatto (E 160b); Beta-Apo-8-Carotenal (E 160e); Beta-Apo-8-Ethyl Ester of Carotene Acid (E 160f); Xanthophylls such as Astaxanthin, Lutein (E 161b); Beta-Carotene (E 160a); Canthaxanthin (E 161g); Carotenoids Carotenes (alpha, beta, gamma, E 160a); Ceres Brown B, Fat Brown B; Chlorophyll, Leaf Green (E 140); Heliogen Blue B, Phthalocyanine Blue; Heliogen Green G, Phthalocyanine Green; Indanthrene Brilliant Red R, D&C Red No. 30; Indigo Dyes such as Indigotine; Irisol; Permanent Carmine FB; and Sudan Yellow 3G, Fat Yellow G. It has been found that these colorants are particularly suitable for hydrophobic silicone. Said colorants are non-charged or anionic with tetraalkylammonium counter ions. They are good soluble in silicone oil and exhibit low toxicity.

The use of colorants preferably permit qualitative or even quantitative indication of the remaining span of life by comparing the actual color of the cushion or member with color wheels or colored diagrams containing in turn indications referring to a time specification. Such time specification may comprise a time specification in days or weeks, for example one, two, three, four, five, six, seven or eight weeks. Also time periods may be indicated on the color wheel or colored diagram, such as two to three weeks, three to four weeks, 10 to 20 days, 20 to 30 days, 30 to 40 days, 40 to 50, days, 50 to 60 days, etc.

According to still another embodiment of the present invention, said colorant is a natural or synthetic food dye. Said food dyes may be non-charged or negatively charged (in case of hydrophilic silicone with anionic detergents), non-charged or positively charged (in case of hydrophilic silicone with cationic detergents), non-charged, positively or negatively charged (in case of hydrophilic silicone with non-ionic detergents), non-charged or anionic with tetraalkylammonium counter ions (in case of hydrophobic silicone).

Several food dyes are contained in the above mentioned lists for colorants and in general may be recognized by their European Number.

According to still another embodiment of the present invention, said food dye is selected from the group consisting of Allura Red AC, Erioglaucine disodium salt, Tartrazine and Fast Green FCF or combinations thereof.

According to a preferred embodiment of the present invention, said member is shared in different regions, each of said regions comprising a different indicator.

In this embodiment the complete member has the same functional material having a predefined functionality that is shared in different regions. In each of said region a different indicator or indicators maybe present. This permits, for example, assessment of the presence of a moisture uptake means in one region and the presence of anti microbial agent in another region. It will be appreciated that there may be any number of regions which preferably correlates with the number of materials having a predefined functionality. For example there may be one, two, three, four, five, six, seven, eight, nine or ten regions or more. The regions may have essentially each shape in each form of boundary between each other. For example in the indicators in the boundary area between two regions may be mixed with each other. In this case indicators with complementary colors may be used to obtain a different color in the boundary area, such as a yellowish (brownish) color in the boundary area if a red and a green indicator has been employed. It will be appreciated that the color depends also from the material used for preparing the mask.

According to still another embodiment of the present invention, each of said regions is adapted to indicate the presence of a functional material having a predefined functionality.

As outlined above each of said regions may provide an individual color for one material of having a predefined functionality.

According to still another embodiment of the present invention, said at least one indicator forms a graphical pattern and/or at least one letter on said member.

In this case the indicator is present in a surface area of the member which has upon top view the shape of a graphical pattern and/or at least one letter. Graphical patterns may comprise essentially each shape, for example a symbol, a small drawing and/or geometric figures. The at least one letter may be derived essentially from each alphabet. It will be appreciated that different letters may be combined to form an understandable word or message informing the user that e.g. replacement of the member is required.

According to an embodiment of the present invention, two or more indicators are present. Each of said two or more indicators may form the secondary color different from the primary colors of each of said two or more indicators.

It will be appreciated that not only one indicator may be employed in correlation with a material of predefined functionality, but rather two or more indicators may be used. In such case one indicator may change its color whereas the others keep the previous color with the result that the visible mixed color changes.

The member for the patient interface may, for example, comprise an alpha olefin sulfonate containing silicone rubber as the material with a predefined functionality in the combination of Brilliant Blue FCF and Fast Green FCF. All three compounds belong to the classes of sulfonates and are therefore expected to be removed from the member in essentially a similar speed. Accordingly in the beginning the member will have a turquoise color with result of the mixing color from blue and green. In case the alpha olefin sulfonate is washed out essentially the same holds true for the two indicators. Accordingly, member which exceeded its span of life has only the color of the material, e.g. plastic material of the member.

Alternatively, an alpha olefin sulfonate containing silicone rubber may be mixed with Brilliant Blue FCF and chlorophylline. Chlorophylline is also a green dye with the consequence that in the beginning the mixing color will be once again turquoise. Since chlorophylline has several carbonate groups its solubility in water is essentially higher than that of Brilliant Blue FCF. Accordingly decrease of alpha olefin sulfonate will first result in a color change from turquoise to blue and then to colorless.

It will be appreciated that use may be taken of any combination of two or more indicators to create not only new colors but also to obtain different coloring effects during loss of a functional material having a predefined functionality.

According to another embodiment of the present invention, the secondary color is a complementary color. Complementary colors exhibit when combined in correct proportions white or black colors. For such a purpose red and green indicators may be employed. An alternative recites in a combination of a blue and orange indicator. The advantage of employing indicators capable of forming complementary colors recites in that the complementary colors may be very well visible. Therefore, the sensitivity for determining a decrease in predefined functionality of said material is high.

According to still another embodiment of the present invention, said at least one material and said at least one indicator are homogenously or evenly distributed in said member.

As outlined above, evenly distributed means that all functions or molecules of the functional material having a predefined functionality and of said indicator have essentially the same distance to each other. Depending on the kind of forces acting between different molecules it may be that there are also agglomerates of several molecules formed. Said agglomerates may be also evenly distributed in the material in the sense that said agglomerates have essentially the same average distance to each other.

Homogenous distribution of said at least one material in said at least one indicator within said member may be easily obtained by mixing the starting compounds of said member together with said at least one material in said at least one indicator before hardening of the member.

According to a preferred embodiment of the present invention, said member is a first member which is connected with a second member through a mechanical release mechanism thereby forming a patient interface for delivering gas to a user.

According to another embodiment of the present invention, said member further comprises other constituents, such as fillers.

The first member may comprise the cushion having the skin contacting material (SCM). The second member comprises the mask shell. This construction facilitates separation of the cushion from the patient interface and thereby washing and in case if required renewal of the same.

BRIEF DESCRIPTION OF THE DRAWINGS

These and other aspects of the invention will be apparent from and elucidated with reference to the embodiment(s) described hereinafter. The following figures and examples are purely illustrative of specific embodiments and should not be understood as limiting the scope of invention. In the following drawings

FIG. 5 schematically illustrates a second embodiment of the patient interface according to the present invention seen from the skin contacting material (SCM).

FIG. 6 schematically illustrates the distribution of functional materials within the skin contacting material (SCM) according to the second embodiment of the present invention.

FIG. 7 schematically illustrates a third embodiment of the patient interface according to the present invention seen from the skin contacting material (SCM).

FIG. 8 schematically illustrates the distribution functional materials within the skin contacting material (SCM) according to the third embodiment of the present invention.

DETAILED DESCRIPTION OF THE INVENTION

Figure 1:
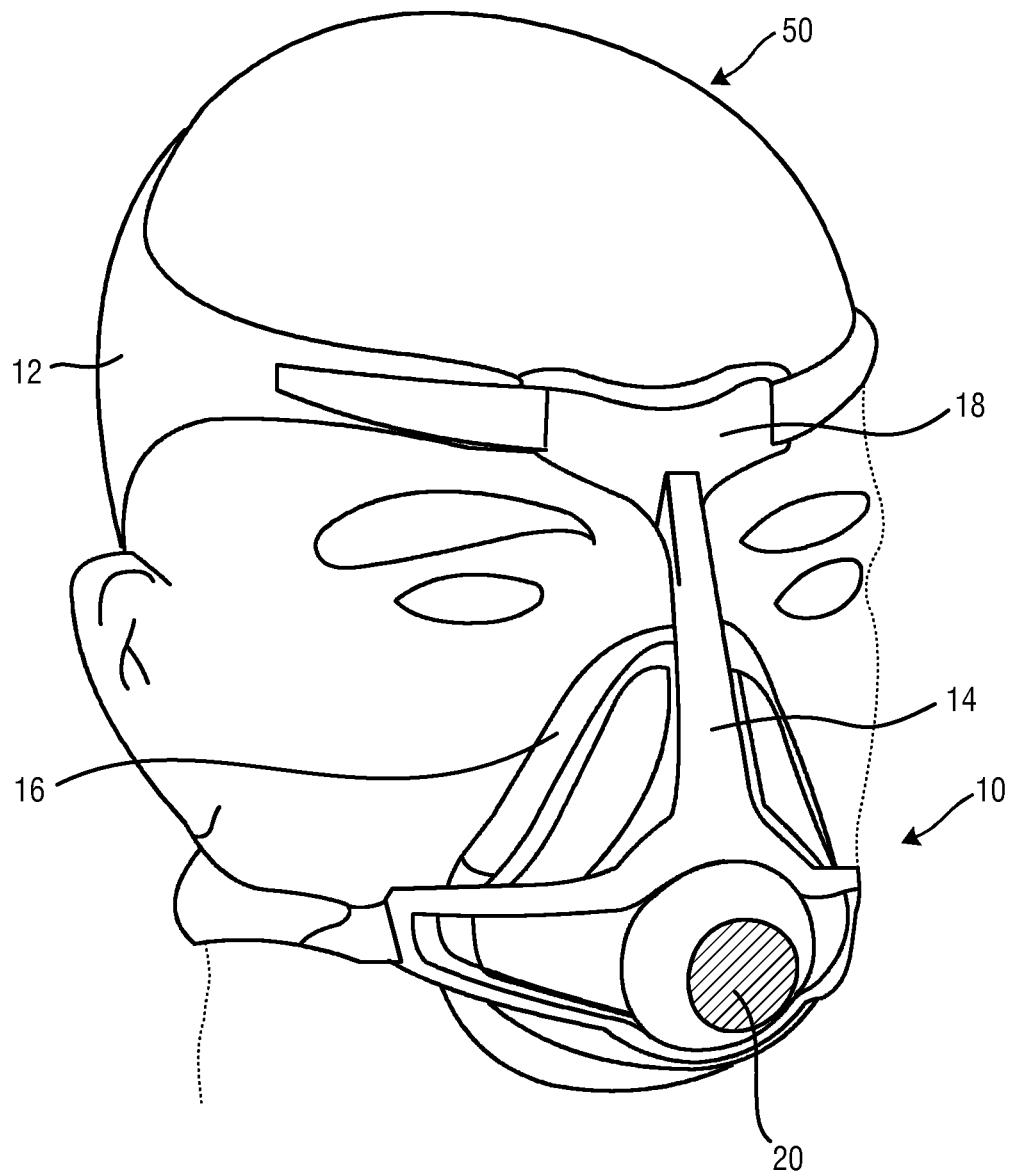
FIG. 1 shows an example of patient interface according to the present invention.

FIG. 1 shows an example of a mask according to the present invention. The main structural elements of the mask shown in FIG. 1 are generally known. The embodiments according to the present invention are shown in FIGS. 2 to 6. However, FIG. 1 shall give an overview of the main structural elements comprised in such a mask.

The mask is in FIG. 1 in its entirety denoted with reference numeral 10. The mask 10, in the following also referred to as patient interface 10, is typically used in pressure support systems (CPAP systems) that supply a flow of gas to the airway of a patient 50. Such patient interfaces are well-known and are mostly worn on the head using a strap system 12 around the patient's head to hold the mask 10 in place around the airway entry features of the human face. The patient interface 10 typically comprises a rigid or semi-rigid mask shell 14 to which the head gear/strap system 12 is attached. The mask shell 14 is usually made of a rigid or semi-rigid material, such as e.g. plastic, polycarbonate or silicone. However, also other materials are generally conceivable. The mask shell 14 serves as a holding frame for holding a flexible or soft cushion/mask flap 16. The cushion/mask flap 16 engages the patient's face when the mask/patient interface 10 is attached to the patient's face during use. It serves as mask-to-patient interface. These cushions 16 are usually made of silicon or comprise one or more gel pads in order to establish a soft contact on the patient's face. A further function of these cushions 16 is the sealing of the interior of the patient interface 10 to the exterior surrounding in order to prevent unwanted air leaks between the patient interface 10 and the patient's face when pressure is supplied to the patient's airway. The shape of the cushion/mask flap 16 is thereto preferably adapted to the shape of the user's face.

The illustrated example refers to a so-called full-face mask 10, wherein the cushion/mask flap 16 surrounds the nose and mouth of the user 50. These full-face masks 10 often comprise an additional cushion support 18, also referred to as forehead support 18, which may be integrally connected to the mask shell 14, and which is arranged to engage the forehead of the patient 50. The additional cushion support/forehead support 18 mainly serves to balance the forces that the mask 10 exerts onto the face of the patient 50 and to mechanically stabilize the mask shell 14 as well as to serve as for a correct and comfortable fit of the mask 10. A gas supplying hose (not shown) is usually connected to a connection interface 20 that is preferably attached to or integrated into the mask shell 14.

As already mentioned above, the example of the patient interface 10 shown in FIG. 1 refers to a so-called full-face mask. It is to be noted that this type of mask is herein included only for illustrative reasons in order to explain the core features of the present invention and make them apparent. However, the present invention is not restricted to any certain type of mask. The present invention may also be applied, for example, for nasal masks, oral masks, total face masks or nasal pillows.

Figure 2A:
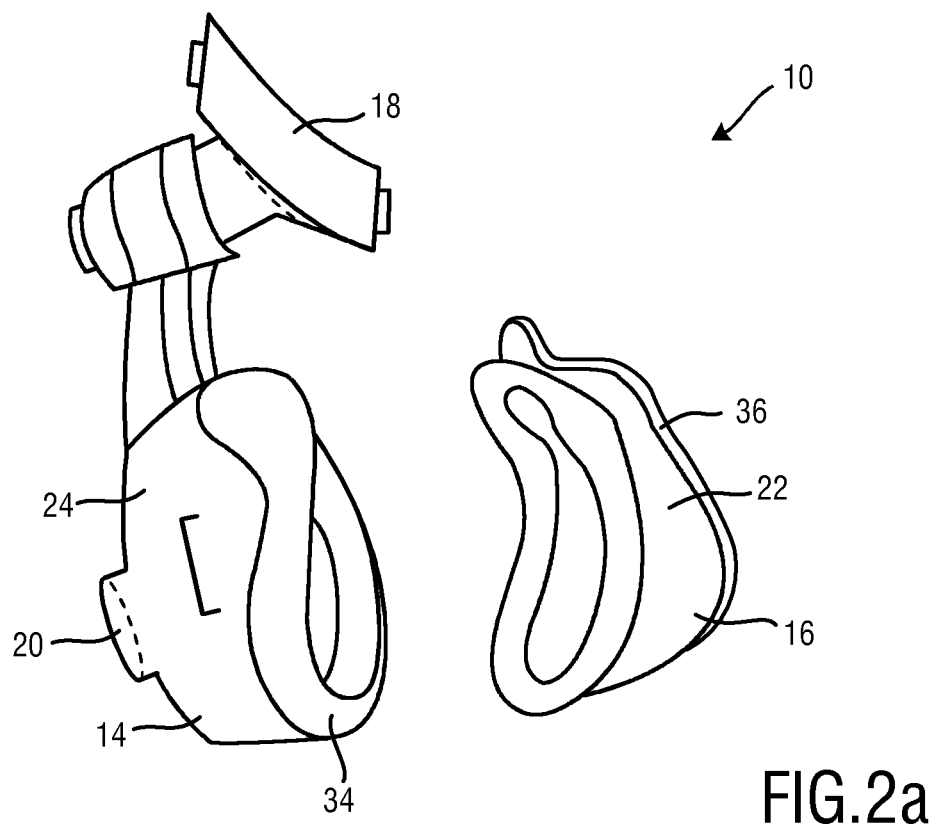
FIGS. 2a and b schematically illustrate a first embodiment of the patient interface according to the present invention.

FIG. 2 shows a first embodiment of the patient interface 10 according to the present invention that overcomes the above-mentioned disadvantages of masks according to the state of the art. Patient interface 10 comprises a first member 22 and a second member 24 that can be connected to each other through a mechanical release mechanism. The first member 22 comprises in this example the cushion/sealing flap 16 or is realized as the cushion/sealing flap 16. The first member 22 exhibits also the skin contacting material (SCM) 36 touching the skin of the user when the mask is used. The first member 22 contains said at least one functional material having a predefined functionality and said at least one indicator (not shown). The second member 24 comprises the mask shell 14 or is realized as the mask shell 14. It shall be noted that the mask shell 14 and the cushion/mask flap 16 are in FIG. 2a shown as two separate parts that are releasable from each other. This is advantageous, since the mask shell 14 and the cushion/mask flap 16 may then be replaced separately from each other, if one of the parts 14, 16 is worn-out. However, it shall be noted that the mask shell 14 may in the alternative also be integrally formed with the cushion/mask flap 16 without leaving the scope of the present invention. Furthermore, it shall be noted that the terms first and second members 22, 24 may also refer to other parts of the mask 10 that can be, but do not have to be releasably connected to each other, e.g. also to the air supplying hose (not shown) and a connection interface 20 (see FIG. 1), i.e. not necessarily as illustrated to the cushion/mask flap 16 and the mask shell 14.

Figure 2B:
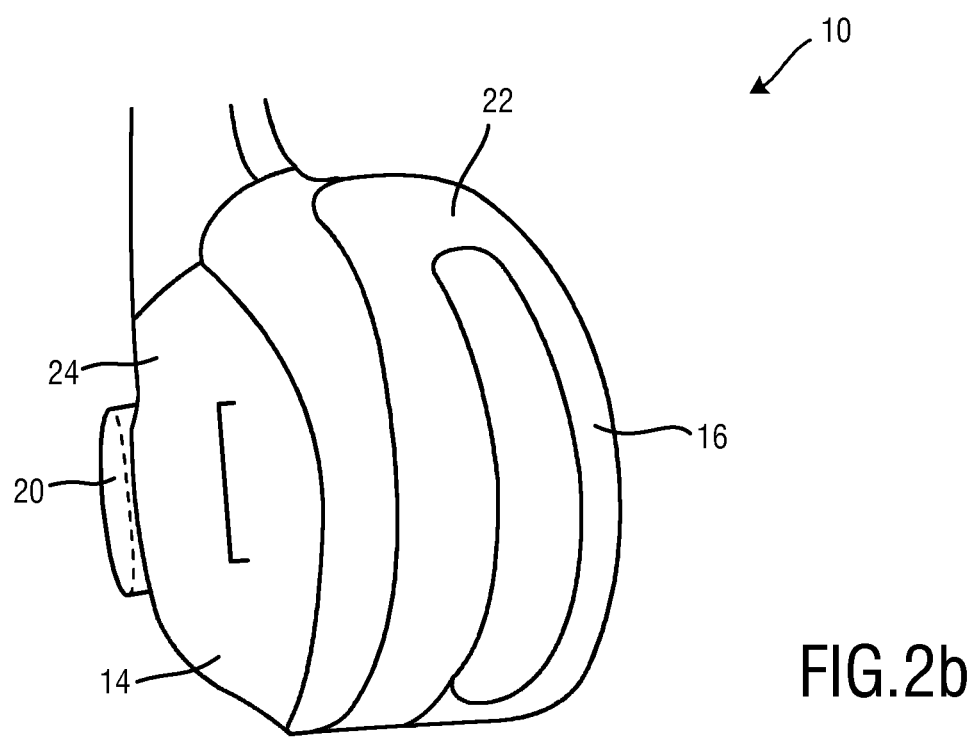

In the illustrated example FIG. 2a shows the disassembled mask 10 wherein the cushion/mask flap 16 or the first member 22 is separated or unconnected from the mask shell 14 or second member 24. The skin contacting material (SCM) is indicated by reference number 36. In contrast thereto FIG. 2b illustrates the situation in which the two members 22, 24 of the patient interface 10 (the cushion/mask flap 16 and the mask shell 14) are connected to each other, i.e. a condition wherein the cushion/mask flap 16 is inserted into the mask shell 14.

FIG. 3-11 refer all patient interfaces 10 having inter alia the cushion 16 with the skin contacting material (SCM) 36 formed or made thereon which applies likewise to the forehead support 18. It will be appreciated that this is no limitation to a particular construction, but rather member 22, cushion/mask flap 16 and skin contacting material (SCM) 36 may form a single piece. Alternatively, member 22 and cushion/mask flap 16 may form a single piece, whereas the skin contacting material (SCM) 36 is formed or made thereon. Still alternatively, cushion/mask flap 16 and skin contacting material (SCM) 36 may form a single piece, whereas the member 22 is formed or made thereon to provide connection to the mask shell 14. Still alternatively, member 22, cushion/mask flap 16 and skin contacting material (SCM) 36 are all discrete elements which may be connected to each other.

Independently therefrom, the skin contacting material (SCM) 36 may be formed or made on the forehead support 18. Alternatively, the skin contacting material (SCM) 36 and the forehead support 18 may be one piece. It will be appreciated that the forehead support 18 may be omitted.

The functional material 32, 34 having a predefined functionality pertains essentially to each kind of active compound, such as drugs or prodrugs, including of which may be beneficial for the user upon wearing the member/patient interface. Two preferred examples of materials 32, 34 having a predefined functionality are (i) moisture uptake means, such as hydrophilic materials capable of taking up and/or absorbing water and which may be either added to the material forming the member or which may be the material used for preparing the member or at least part thereof, and (ii) anti microbial agents. It will be understood that the representation of e.g. hydrophilic material by circles in the figures is not to be understood as limiting but rather schematically highlights the function of the e.g. hydrophilic material.

The moisture uptake means may refer to any material capable of taking up or adsorbing moisture and may comprise for example a hydrophilic material or a hydrophobic material. The hydrophilic silicone may be processed out of a mixture of a standard silicone and an addition of alpha olefin sulfonate.

The anti microbial agents may prevent bacteria growth and a biofilm formation on the skin contacting material (SCM) 36, which could likewise lead to skin infections, inflammation or other bacteria-induced infections such as pulmonary infections or infections of the respiratory system through biofilms present on mask materials and entering the respiratory system during use of CPAP. Anti microbial agents comprise inter alia quorum sensing inhibitors and antibiotics, but also other substances toxic for particular microorganisms, such as finely divided silver. Quorum sensing inhibitors are particularly preferred in the present embodiments. Quorum sensing inhibitors block the microbial communication and may prevent the symbiosis of microbes with its own species as well as with other species and regulates the expression of genes involved in biofilm formation, antibiotic production, expression of virulence. Examples of particularly preferred quorum sensing inhibitors comprise halogenated furanone compounds or furanone derivatives in general.

Figure 3:
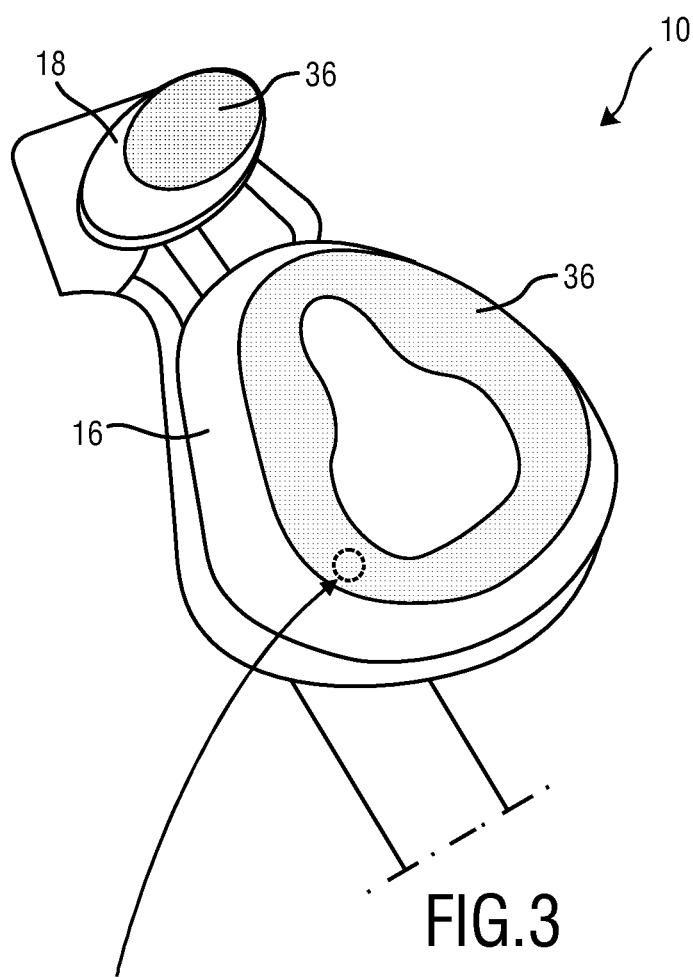
FIG. 3 schematically illustrates the first embodiment seen from the skin contacting material (SCM). The SCM with predefined functionality may be a colored hydrophilic silicone or a colored, non-biofouling hydrophobic silicone.

FIG. 3 represents another view on the mask 10 wherein the skin contacting material (SCM) 36 can be seen more in detail. The material skin contact are 36 is in this example made on the cushion/mask flap 16. In this embodiment also the skin contacting material (SCM) 36 is made on the forehead support 18. As outlined above, this shall be not understood as limitation to the present construction. In the skin contacting material (SCM) 36 of the cushion/mask flap 16 and/or the forehead support 18 a functional material 32 having a predefined functionality may be employed. As outlined above the functional material 32 may be a compound added to the material forming said member 22. Preferably, the functional material 32 may be a constituent of said member, i.e. a part of the member 22 or the complete member 22 which is made of the functional material. Furthermore, at least one indicator 30 may be employed in the skin contacting material 36. The concentration of said at least one indicator 30 is preferably correlative with the predefined functionality of said at least one functional material 32. In other words, this means that as soon as the material 32 having a predefined functionality is reduced, washed out, or looses its functionality the at least one indicator will be reduced or lost as well or at least changes its visual appearance. In this way the user may receive a visual indication by means of the at least one indicator 30 if the predefined functionality of said at least one functional material 32 is reduced or completely lost, e.g. due to wear-out of patient interface 10.

In said example, said at least functional material 32 is a hydrophilic material, such as hydrophilic silicone processed out of a mixture of standard silicone and addition of alpha olefin sulfonate, and the said at least one indicator 30 is one of the colorants outlined above, such as Fast Green FCF. The functional material 32 improves the moisture uptake behavior of the patient interface 10 which is specifically important for improving the comfort of the patient 50 and for preventing a moisture accumulation at the skin contact area 36, which could lead to skin irritations and/or skin damages. The at least one indicator or colorant 30 helps to visually indicate the user that one or both material have lost their function at least to some extent. Thereby the user receives a feedback when to replace the patient interface 10 or at least parts of it, e.g. the cushion/mask flap 16.

It will be appreciated that any combination of one or more of the above mentioned materials 32 having a predefined functionality may be encompassed by the present invention and are also suitable to put the present invention into practice. As outlined above the functional material 32 may be a compound added to the material forming said member 22. Alternatively, the functional material 32 may be a constituent of said member, i.e. a part of the member 22 or the complete member 22 is made of the functional material. The same holds true for the indicator(s) 30 employed. Further examples for suitable functional materials 32 and indicators 30 have been mentioned in the summary of the invention.

Figure 4:
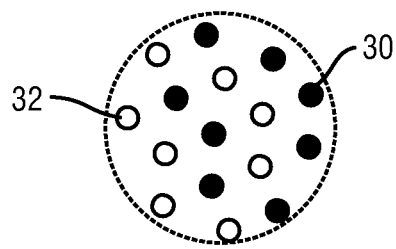
FIG. 4 schematically illustrates the distribution of functional materials within the skin contacting material (SCM) according to the first embodiment of the present invention.

FIG. 4 schematically illustrates the distribution of functional materials within the skin contacting material (SCM) 36 shown in FIG. 3. Indicator molecules 30 and the functional material 32 having a predefined functionality are evenly distributed or embedded in the material forming the skin contacting material (SCM) 36 which is the same like the material forming the cushion/mask flap 16 or first member 22 and which may be a silicone rubber.

FIGS. 5 and 6 corresponds essentially to FIGS. 3 and 4. The only difference is that instead of functional material 32 another functional material 34 has been employed (see FIG. 5) which is a quorum sensing inhibitor which may be mixed into the polymer, such as a hydrophobic silicone, which is present at least in the skin contacting material (SCM) 36. The indicator 30 may be the same as for the first embodiment, i.e. Fast Green FCF. It will be however appreciated that based on the selection of another functional material 34 another indicator 30 may be employed. FIG. 6 indicates that functional material 34 and indicator 30 are homogenously distributed within the skin contacting material (SCM) 36.

FIGS. 7 and 8 corresponds essentially to FIGS. 3 and 4. The difference resides in that a combination of indicator 28 and indicator 30 has been employed (see FIG. 7). Functional material 32 is a hydrophilic silicone processed out of a mixture of standard silicone and addition of alpha olefin sulfonate, but may be however also a quorum sensing inhibitor mixed into a polymer or a combination of standard silicone, alpha olefin sulfonate and quorum sensing inhibitor. As noted above representation of e.g. hydrophilic silicone by circles in the figures is not to be understood as limiting but rather highlights the function of the e.g. hydrophilic silicone. The indicator 30 may be the same as for the first and second embodiment or different. Indicator 28 differs from indicator 30. In the present example the indicator 30 is Fast Green FCF and the indicator 28 is Allura Red AC. FIG.

8 indicates that functional material 32 and indicators 28/30 are homogenously distributed within the skin contacting material (SCM) 36.

Figure 9:
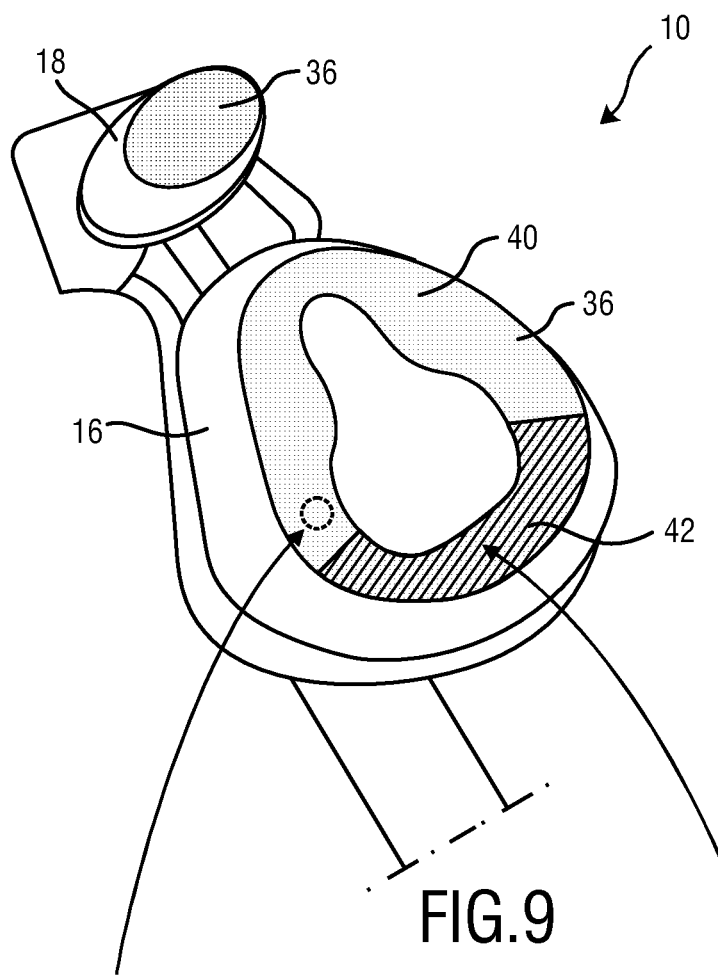
FIG. 9 schematically illustrates a fourth embodiment of the present invention.

The embodiment shown in FIG. 9 indicates two regions 40, 42 made in the skin contacting material (SCM) of the cushion/mask flap 16 or first member 22. The material of the skin contacting material (SCM) 36, the cushion/mask flap 16 or first member 22 may be once again a silicone rubber. Sodium alpha-olefin sulfonate may be employed as functional material 30 having a predefined functionality. In the present example two indicators 28 and 30 have been employed. The first indicator may be Allura Red AC and a second indicator may be Fast Green FCF. The first indicator is present in the region 40 exclusively whereas the second indicator 30 is present in the other region 42 exclusively. It will be appreciated that the indicators and materials having a predefined functionality serve for illustrating purposes only.

Figure 10A:
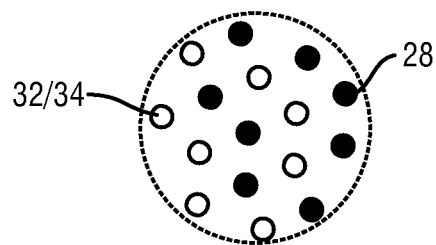
FIGS. 10a and b schematically illustrate distribution of a functional material having a predefined functionality and an indicator for different regions according to the fourth embodiment.

FIG. 10a show that in the first region 40 indicated in FIG. 9 for example Allura Red AC as first indicator 28 and for example sodium alpha-olefin sulfonate molecules forming the material 32, 34 having a predefined functionality are employed. The molecules of the indicator 28 and of the material 32, 34 having a predefined functionality may be evenly distributed or embedded in the material forming the skin contacting material (SCM) 36, cushion/mask flap 16 or first member 22.

Figure 10B:
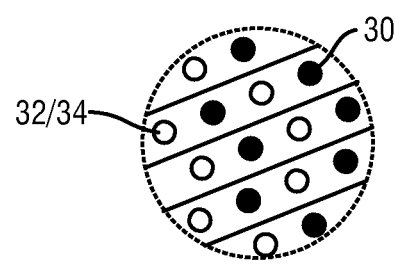

Likewise to FIG. 10a, FIG. 10b shows that a second indicator 30 and material 32, 34 having a predefined functionality are present in the region 42. Once again the molecules 28 and 30 may be evenly distributed or embedded within the material forming the skin contacting material (SCM) 36, cushion/mask flap 16 or first member 22. The exemplary use of two indicators of complementary colors (red and green) in different regions 40, 42 of the skin contacting material (SCM) 36 permits improved possibility to the user to recognize when the material 32, 34 having a predefined functionality is essentially washed out of the skin contacting material (SCM) 36, cushion/mask flap 16 or first member 22. The use of two color indicators, especially the use of two complementary colors may be more easily prosecuted by employing a color wheel (not shown). It may be of particular advantage to employ indicators of complementary colors which are washed out at different speeds.

Figure 11:
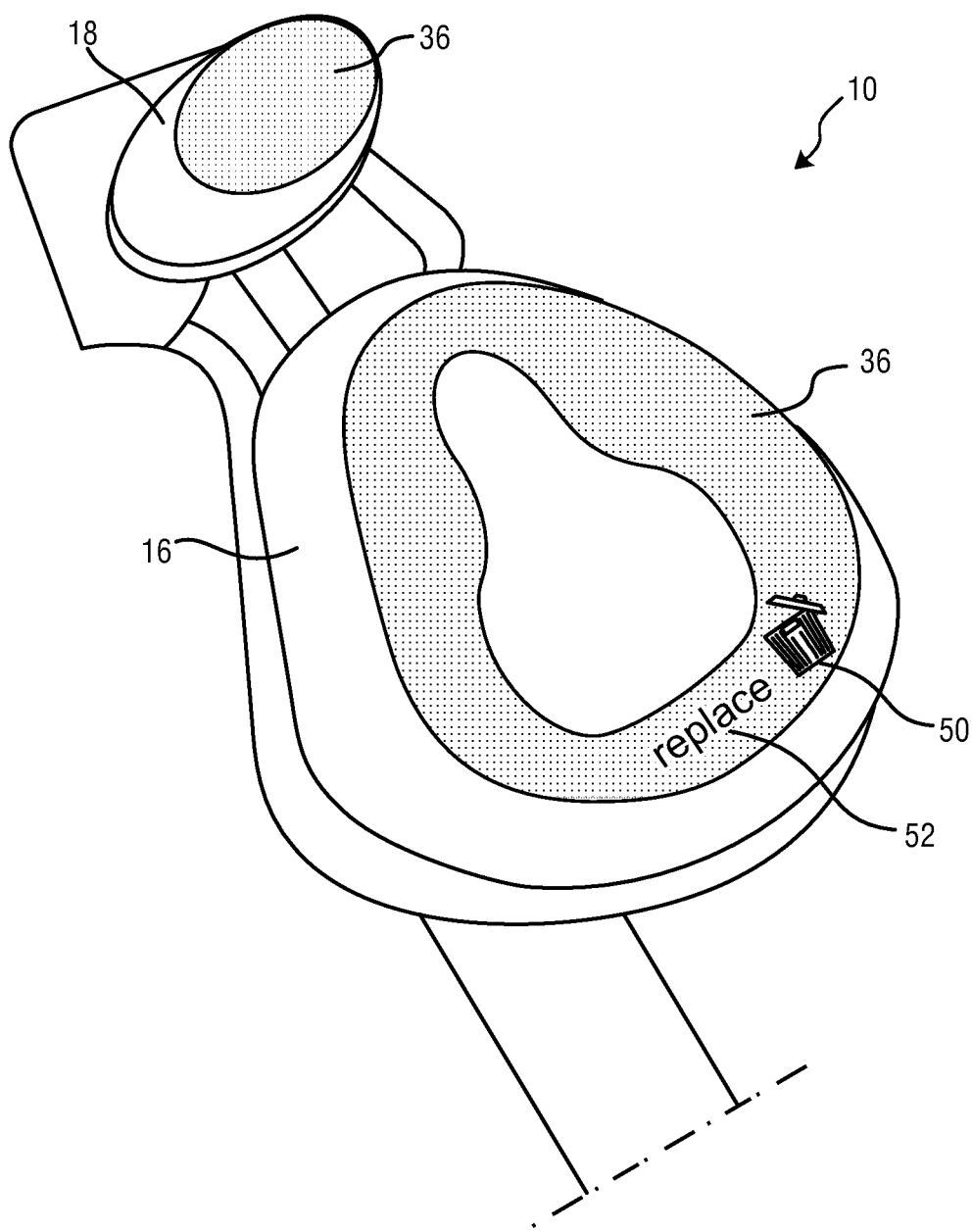
FIG. 11 schematically illustrates a fifth embodiment of the present invention wherein in the skin contacting material (SCM) letters and symbols are provided.

In the embodiment shown in FIG. 11 the skin contacting material (SCM) 36 may be provided with a symbol 50 and message 52 having letters forming the word "replaced". Symbol 50 and message 52 are only visible in case the cushion/mask flap 16 or first member 22 needs to be replaced. This may be obtained essentially in two ways. The first resides in forming the symbol 50 and/or a message 52 below the surface of the skin contacting material (SCM), for example in depth of up to 6 mm. However, the symbol 50 and/or a message 52 may be made at other distances from the surface, for instance 50 μm to 6 mm, 1 to 5 mm, 1 to 4 mm, 2 to 4 mm and 3 to 4 mm, 500 μm to 1 mm, 200 μm to 500 μm, 100 μm to 300 μm, 50 μm to 100 μm. Likewise to the first embodiment, the skin contacting material (SCM) 36, cushion/mask flap 16 or first member 22 is provided with a material having a predefined functionality and an indicator. The concentration of the indicator as well as its color are chosen in a manner that its color completely covers the symbol 50 and message 52. With increasing usage time and washing of the first member 22 or cushion/mask flap 16, the concentration of the indicator decreases in parallel/simultaneously to the predefined functionality of said functional material which is reduced either due to washing out or decomposition. If the concentration of the indicator is low enough and its color has disappeared to a sufficient degree symbol 50 and message 52 will be visible to the user and indicate replacement need due functionality change.

Alternatively, the entire skin contacting material (SCM) 36, cushion/mask flap 16 or first member 22 may consist of the material having a predefined functionality. Symbol 50 and message 52 may be made with one or more indicators. In case only one indicator is used disappearance of the symbol 50 and message 52 occurs due to reduced concentration of the indicator which correlates with the loss of the predefined functionality of said functional material. Disappearance of the symbol 50 and message 52 thereby indicates that replacement is required. The use of two indicators of different solubility may be used to indicate by a color change of the symbol 50 and message 52 that replacement is required. First and second indicator originally form a mixing color (third color). Due to accelerated washing out of the indicator of higher solubility in water the second indicator remains in the material, having a different color than the mixing color.

In order to realize a cushion that takes up moisture and comprises also an indicator at what time to replace the cushion, preferably hydrophilic silicone is processed to form a cushion. The hydrophilic silicone is processed out of a mixture of a standard silicone and an addition of alpha olefin sulfonate. The hydrophilic silicone cushion takes up moisture from the patient's skin and improves in this manner patient comfort and reduces risk for red mark formation. In this case, the indicator is a color change indicator. For example, daily washing of colored hydrophilic silicone materials as suggested in examples 2 and 4 below will show that the red dye is washed out in parallel to decreasing concentrations of alpha-olefin sulfonate which may be assessed and validated by standard gas chromatography, liquid chromatography, IR spectroscopic, or digital color measurements well known instrumentation techniques.

The following examples serve to underpin workability and technical feasability of the present invention and shall not be construed as limiting. It will be appreciated that any material combination of the above mentioned compounds/constituents is feasible and may be used to put the present invention into practice.

EXAMPLES

Example 1

A hydrophilic silicone cushion employed may be prepared from a formulation with Elastosil LR3004/40:

12 g of sodium alpha-olefin sulfonate (BIO-TERGE® AS-90 BEADS, Stepan Company Northfield, Ill., United States) was mixed 3 to 4 times with 7 g of (1:1) ethanol and water. Afterwards 19 g of Elastosil LR 3004/40 A (Wacker Silicones, Germany) were added and mixed for two times. Subsequently water and ethanol were removed until about 0.5 g of the water/ethanol phase still remained resulting in good mixing with component B and no agglomerates. The solvents were removed under vacuum and at a temperature of 70 to 80° C. for several hours until the solvents were removed to the desired degree. The solution was gently mixed during evaporation.

26 g of Elastosil 3004/40B were added and mixed two to three times until a homogenous mixture was obtained. The ratio A:B was 1:1.37 and the ratio (A+soap):B is 1.19:1. The mixture was processed in a mold for 20 min at a temperature between 130 and 140° C. If required post-curing under vacuum at a temperature of about 130° C. for one hour may be employed.

Example 2

0.2 g Allura Red AC were dissolved in 7 g of (1:1) ethanol and water and subsequently mixed 3 to 4 times with 12 g of sodium alpha-olefin sulfonate (BIO-TERGE® AS-90 BEADS, Stepan Company Northfield, Ill., United States). Afterwards 19 g of Elastosil LR 3004/40 A (Wacker Silicones, Germany) were added and mixed for two times. Subsequently water and ethanol were removed until about 0.5 g of the water/ethanol phase still remained. This procedure results in good mixing with component B and no agglomerates. The solvents were removed under vacuum and at a temperature of 70 to 80° C. for several hours until the solvents were removed to the desired degree. The solution was gently mixed during evaporation.

26 g of Elastosil 3004/40B were added and mixed two to three times until a homogenous mixture was obtained. The ratio A:B was 1:1.37 and the ratio (A+soap):B is 1.19:1. The mixture was processed in a mold for 20 min at a temperature between 130 and 140° C. If required post-curing under vacuum at a temperature of about 130° C. for one hour may be employed.

Example 3

In this example the commercial silicone elastomer Elastosil LR 3003/5 (commercially available from Wacker Silicones, Germany) was used as the silicone precursor material. The silicone precursor material is a two component system that was normally mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups. A commercial sodium alpha-olefin sulfonate RCH=CH(CH$_2$)nSO$_3$Na (n=12-14) from Stepan Company (Northfield, Ill., United States) was used. 12 g of this very fine powder (particle sizes below 400 μm) was mixed with 7 g of ethanol and water mixture (50/50% by weight). Then 19 g of the A component of the silicone precursor material was added and mixed with a speed mixer. After mixing the ethanol and water were removed under vacuum at 60° C. until a small residual amount (approximately 0.5 gram) of water was still present. Then silicone precursor B component (24.7 g) was added and the obtained composition was mixed. The commercial sodium alpha-olefin sulfonate added to the silicone precursors A+B, is thus amounting to 27.5 weight % of silicone precursor (A+B) weight ((weight sodium alpha-olefin sulfonate/weight silicone A+B)*100). The mixing ratio of this system for component A to B was 1 to 1.3. Material samples were prepared by pressure molding at 130° C. for 10 to 15 minutes at 711 psi (approximately 49 bar). If required, post curing under vacuum at a temperature of about 130° C. for one hour may be employed Example 4

This example corresponds to example 3 above with the exception that to the 7 g of water ethanol mixture (50/50% by weight) 0.2 g Allura Red AC have been added and dissolved therein.

While the invention has been illustrated and described in detail in the drawings and previous description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A member for a patient interface, said member comprising:
    a skin contacting material in contact with skin of a patient, comprising:
        at least one functional material homogeneously distributed or embedded in the skin contacting material effective for moisture uptake of the member, comprising:
            a hydrophilic polymer; and
            an alpha olefin sulfonate; and
        a concentration of at least one indicator comprising a colorant, wherein the concentration of said at least one indicator in said member correlates with the moisture uptake in the member, and wherein the concentration of said at least one indicator decreases when the concentration of the alpha olefin sulfonate decreases which correlates to a decrease in the moisture uptake in the member.

2. Member for a patient interface according to claim 1, wherein said hydrophilic polymer comprises silicone rubber.

3. Member for a patient interface according to claim 1, wherein said at least one functional material further comprises a quorum sensing inhibitor.

4. Member for a patient interface according to claim 1, wherein said colorant is a natural food dye or synthetic food dye.

5. Member for a patient interface according to claim 4, wherein said food dye is selected from the group consisting of Allura Red AC, Erioglaucine disodium salt, Tartrazine and Fast Green FCF or combinations thereof.

6. Member for a patient interface according to claim 1, wherein said member further comprises different regions, each of said regions comprising a different indicator of said at least one indicator.

7. Member for a patient interface according to claim 6, wherein each of said regions is adapted to indicate presence of one functional material of said at least one functional material.

8. Member for a patient interface according to claim 1, wherein said at least one indicator forms a graphical pattern and/or at least one letter on said member.

9. Member for a patient interface according to claim 1, wherein two or more indicators of said at least one indicator comprising primary colors are present, wherein said two or more indicators form a secondary color different from the primary colors of each of said two or more indicators.

10. Member for a patient interface according to claim 9, wherein the secondary color is a complementary color.

11. Member for a patient interface according to claim 1, wherein said member is a first member which is connected with a second member through a mechanical release mechanism, thereby forming said patient interface for delivering gas to the patient.

12. Member for a patient interface according to claim 1, wherein the skin contacting material is part of a cushion for contacting a face of the patient, a forehead support, or a mask shell.

13. The patient interface for delivering gas to the patient comprising the member according to claim 1.

* * * * *